United States Patent [19]

Fenster et al.

[11] Patent Number: 4,555,728
[45] Date of Patent: Nov. 26, 1985

[54] DIGITAL FLUOROGRAPHY

[75] Inventors: Paul Fenster, Petah Tikvah; Zvi Netter, Haifa; Yair Shimoni, Jerusalem, all of Israel

[73] Assignee: Elscint Ltd., Haifa, Israel

[21] Appl. No.: 546,177

[22] Filed: Oct. 27, 1983

[30] Foreign Application Priority Data

Nov. 26, 1982 [IL] Israel ..................................... 67344

[51] Int. Cl.[4] .............................................. H04N 5/32
[52] U.S. Cl. ...................................... 358/111; 378/99
[58] Field of Search ....................... 358/111; 364/414; 378/99, 96, 101, 105, 106, 108, 97, 98, 111; 250/315.3

[56] References Cited

U.S. PATENT DOCUMENTS 4,482,918 11/1984 Keyes et al. ..................... 378/99 X Primary Examiner—Howard W. Britton
Assistant Examiner—Victor R. Kostak
Attorney, Agent, or Firm—Sandler & Greenblum

[57] ABSTRACT

A system for converting video camera images, obtained when the camera scans radiation generated images, to frames of electrical signals; the radiation generated images are obtained responsive to pulses applied to activate a radiation source during pulse periods; the system applies the pulses at a rate of at least 15 per second and means are provided for reading out the frames at a rate of at least 15 per second.

34 Claims, 7 Drawing Figures

DIGITAL FLUOROGRAPHY

BACKGROUND OF THE INVENTION

The present invention relates to object examining systems, and to methods of operating such systems. The invention is particularly applicable to imaging objects by digital fluorography, and is therefore described below with respect to such application.

Digital fluorography systems are commonly operated according to either a dynamic mode for fast moving objects, or according to a static mode for stationary or slow moving objects.

In the dynamic mode, the X ray exposure is usually continuous, and the readout is usually interlaced to avoid flicker. The interlaced system used in the U.S.A. is a 525 line system, producing 30 frames/second, each frame including two interlaced fields; the interval for each field is approximately 14.5 ms, and each field is separated by blanking pulses of approximately 1⅓ ms during the retrace intervals. The European system is a 625 line system with the blanking pulses during the retrace intervals being about 1.6 ms. In both systems, the initial images are of limited utility because at least one frame, and usually several frames, are required to allow the video signal level to stabilize. Thus, while this dynamic mode can image fast moving objects at a frame rate of 25 or 30 frames per second without flicker, it has the disadvantage of limited contrast because of the limited dosage permitted by the continuous X ray exposure.

The static mode is commonly used for imaging non moving or slow moving objects wherein a dynamic presentation at 25 or 30 frames per second is not required. In this mode, the X-ray source is periodically pulsed to expose the object, and the readout is usually a progressive one rather than an interlaced one. This is because an interlaced readout has smaller dose efficiency in view of the unavailability of the initial frames, and also lacks flexibiity in the choice of exposure time in view of the constraints of the X ray exposures to multiples of the TV frame time. Thus, while the pulse mode permits greater dosage, its main disadvantage is that it is useful only in non moving or slow moving objects as mentioned above.

An object of the present invention is to provide a new method and apparatus for examining objects, and particularly for imaging objects of digital fluorography, which new method and apparatus enables attaining higher frame rates than the conventional pulsed (static) mode, while at the same time enabling higher dosage, and therefore greater contrast, than the conventional continuous (dynamic) mode.

BRIEF SUMMARY OF THE INVENTION

According to one broad aspect of the present invention, there is provided a method of examining an object by repeatedly exposing same to a source of penetrating radiation, converting the radiation transmitted though the object to a pattern of electrical charges on the mosaic of a TV camera, and repeatedly scanning the mosaic by an electron beam controlled by scanning signals to read out during scanning intervals electrical signals representing frames of the object examined, which scanning signals are separated by blanking signals for blanking the TV camera during the retrace intervals between readout frames; characterized in that the source of penetrating radiation is energized by exposure pulses applied during the retrace intervals concurrently with the blanking signals.

In the preferred embodiments of the invention described above, each readout field is followed by a scrub field effected during the subsequent trace, in which the mosaic is scanned to scrub out the electrical charges of the preceding readout field.

As to be more particularly described below, the scanning intervals are shortened, and the exposure pulses are applied to the radiation source for an exposure period greater than the retrace intervals of a conventional TV camera scanning system. For example, in the described embodiment the interval available for X-ray pulsing is increased from about 1 ms to about 3.5 ms. Particularly effective results have been produced when the retrace intervals are increased to slightly more than 3 ms, and the exposure pulses are applied for an exposure period of approximately 3 ms.

According to another broad aspect of the present invention, there is provided apparatus for examining an object, comprising:

a source of penetrating radiation, energizing means for energizing the source to expose the object to the radiation, a TV camera tube having a mosaic and means for generating an electron beam, converting means for converting the radiation transmitted through the object, upon exposure to the radiation of the source, to a pattern of electrical charges on the mosaic of the TV camera tube, and scanning means producing scanning signals for displacing the electron beam of the TV camera tube to cause same to scan the mosaic to read out, during scanning intervals, electrical signals representing frames of the object being examined, the scanning means also producing blanking signals for blanking the TV camera tube during the retrace intervals between frames, characterized in that the energizing means for energizing the source of penetrating radiation is controlled by exposure pulses applied during the retrace intervals concurrently with the blanking signals.

As will be more particularly described below, the invention enables attaining higher frame rates than in the conventional pulsed (static) mode in order to better image moving objects, such as the coronary arteries, and at the same time it permits exposing the patient to the X-rays for smaller exposure periods than the above described continuous (dynamic) mode, thereby enabling larger exposure dosages.

Further features and advantages of the invention will be apparent from the description below.

BRIEF DESCRIPTION OF THE DRAWINGS

The invention as herein described, by way of example only, with reference to the accompanying drawings, wherein.

THE PRIOR ART

Figure 1:
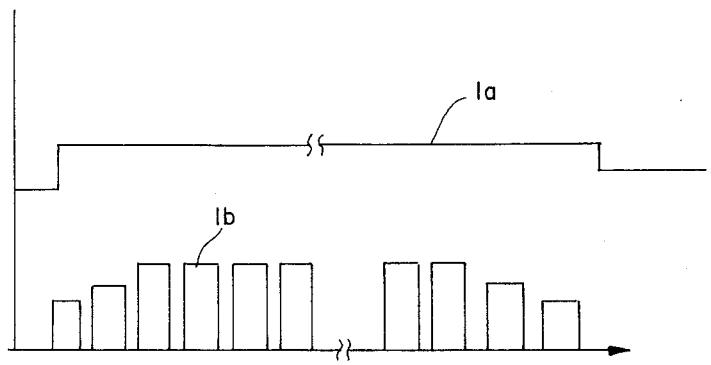
FIG. 1 is a diagram illustrating the operation of a known dynamic digital fluorography system including a continuous X-ray exposure and an interlaced readout.

FIG. 1 diagrammatically illustrates the operation of a conventional digital fluoroscopic apparatus utilizing a continuous X-ray exposure 1a and an interlaced TV readout 1b. Because the X-ray exposure 1a is continuous, it must be at a relatively low level, for example 10 ma, and is applied for a substantial period of time, for example 10–20 seconds. To avoid flicker, the TV readout 1b should be at about 25 or 30 frames per second, there being two interlaced fields for each frame. As indicated above, in the U.S.A. 525 line system, there are 30 frames per second with each field constituted of 241½ lines and being about 14.5 ms; with the blanking pulses for each field being approximately 1⅓ ms; and in the European 625 line system, each frame includes two interlaced fields each of 287.5 (live) lines, the blanking pulses being approximately 1.2 ms.

As shown in FIG. 1, the initial fields and frames are of lower magnitude than the others because of the time required for the video signal level to stabilize and by the charge build up time or lag of the TV pickup tube. This applies not only to an interlaced readout, but also to a progressive readout using a continuous exposure, and therefore the initial frames in a continuous mode of operation are of limited utility. However, this limited utility of the initial frames is of little concern in a continuous mode of operation since the examination is generally conducted for a relatively substantial period of time, i.e. 10–20 seconds as mentioned above.

As also mentioned above, the conventional continuous mode of operation illustrated by FIG. 1 is commonly used in examining moving objects wherein at least 25–30 frames per second are required in order to avoid flicker. The drawback in the continuous mode of operation, however, is that because of the continuous exposure, the dose per frame must be relatively low, and therefore the contrast is relatively low.

Figure 2:
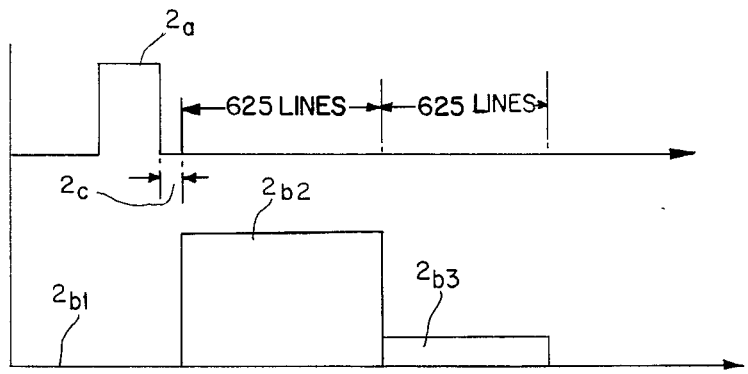
FIG. 2 is a diagram illustrating the operation of the known system including the pulsed X-ray exposure with a progressive readout.

When examining static or slow moving objects, a dynamic acquisition at 25 or 30 frames per second is not required, and therefore the apparatus may be operated according to the conventional pulsed mode as illustrated in FIG. 2. In this mode, the X-ray is periodically energized by an exposure pulse, indicated at 2a in FIG. 2. The TV readout may be either interlaced or progressive. The progressive readout is more commonly used, this being illustrated in FIG. 2, because in an interlaced readout the second field has only about 10–20% the magnitude of the first, and therefore the separation of the X-ray exposure from the TV readout is very difficult to achieve.

This disadvantage, as well as others, is avoided by using a progressive readout with a pulse exposure mode, which is the operation illustrated in the diagram of FIG. 2. In the European 625 line system, there is a single scan readout 2b2 of the target following the X-ray exposure 2a, which provides a frame of uniform brightness and avoids the charge build up problems of the continuous mode. The read frame 2b2 is followed by a scrub frame readout 2b3 to remove any charge remaining on the target prior to the next expose and read sequence. The scrub frame 2b3, following th readout frame 2b2, is only a few percent of the magnitude of the latter, as mentioned earlier.

In the conventional pulsed exposure progressive readout operation illustrated in FIG. 2, the exposure pulse 2a is applied during a blanking period 2a within the blanked frame interval 2b1 of the TV readout during the frame before the read frame. Thus, the maximum rate of operation in this mode is one third (⅓) the frame rate.

DESCRIPTION OF PREFERRED EMBODIMENTS OF THE INVENTION

Figure 3:
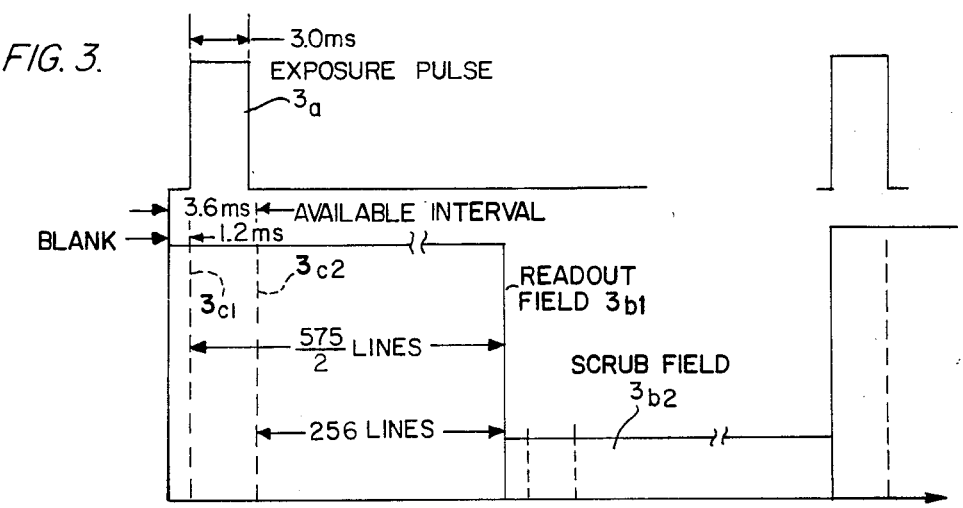
FIG. 3 is a diagram illustrating the operation of a system in accordance with the present invention based on a pulsed X-ray exposure and a interlaced readout.

FIG. 3 diagrammatically illustrates the operation of the apparatus in accordance with one embodiment of the present invention wherein the X-ray source is energized by exposure pulses applied during the retrace intervals concurrently with the blanking signals of the TV readout. Thus, as known, the TV camera tube includes a target which receives a pattern of electrical charges according to the object being imaged. The conventional TV camera tube further includes an electron gun for generating an electron beam, and scanning means displacing the electron beam to cause the beam to scan the target to read out, during scanning intervals, electrical signals representing frames of the object being imaged. The conventional TV camera further generates blanking signals for blanking the beam during the retrace intervals between frames. Thus, in the 625 line European system, the blanking pulses are approximately 1.6 ms, and in the 525 line U.S.A. system they are approximately 1.33 ms. FIG. 3 illustrates the operation in accordance with the present invention of the European 625 line system having blanking pulses of 1.2 ms.

Thus, as shown in FIG. 3, since only 256 lines are needed for a 256×256 information matrix, the blanking pulse for a readout field 3b1, which is conventionally of 1.6 ms duration as indicated by by broken line 3c1, is lengthened to 3.6 ms as shown by broken line 3c2. Alternatively, the blanking pulse can remain the same but the X-ray pulse can be lengthened to include the non active lines. This lengthening of the effective retrace interval will in turn shorten the scanning interval from 575/2 line lines to 256 line lines, as also indicated in FIG. 3a. The exposure pulse 3 which energizes the X-ray tube is applied during this lengthened interval hereinafter sometimes called the "available interval". It has been found that a 3.0 ms exposure pulse 3a is sufficient to provide the required dosage and to be accommodated within the lengthened 3.6 ms interval.

Each readout field 3b1 is followed by a scrub field 3b2 to remove any charges remaining on the target prior to the next expose and read sequence, as described above. As also described above, the scrub field 3b2 has only 10–20% the magnitude of the readout field 3b1.

If desired, either or both the "data" or the scrub field can use a wider beam in order to assure removal of any charge remaining on the target prior to the next expose and read sequence. This can easily be effected by providing a resistor, for example, connected in circuit with the focus coil of the TV camera, which resistor is switched in and switched out in order to increase the beam width during the scrub field.

Figure 4:
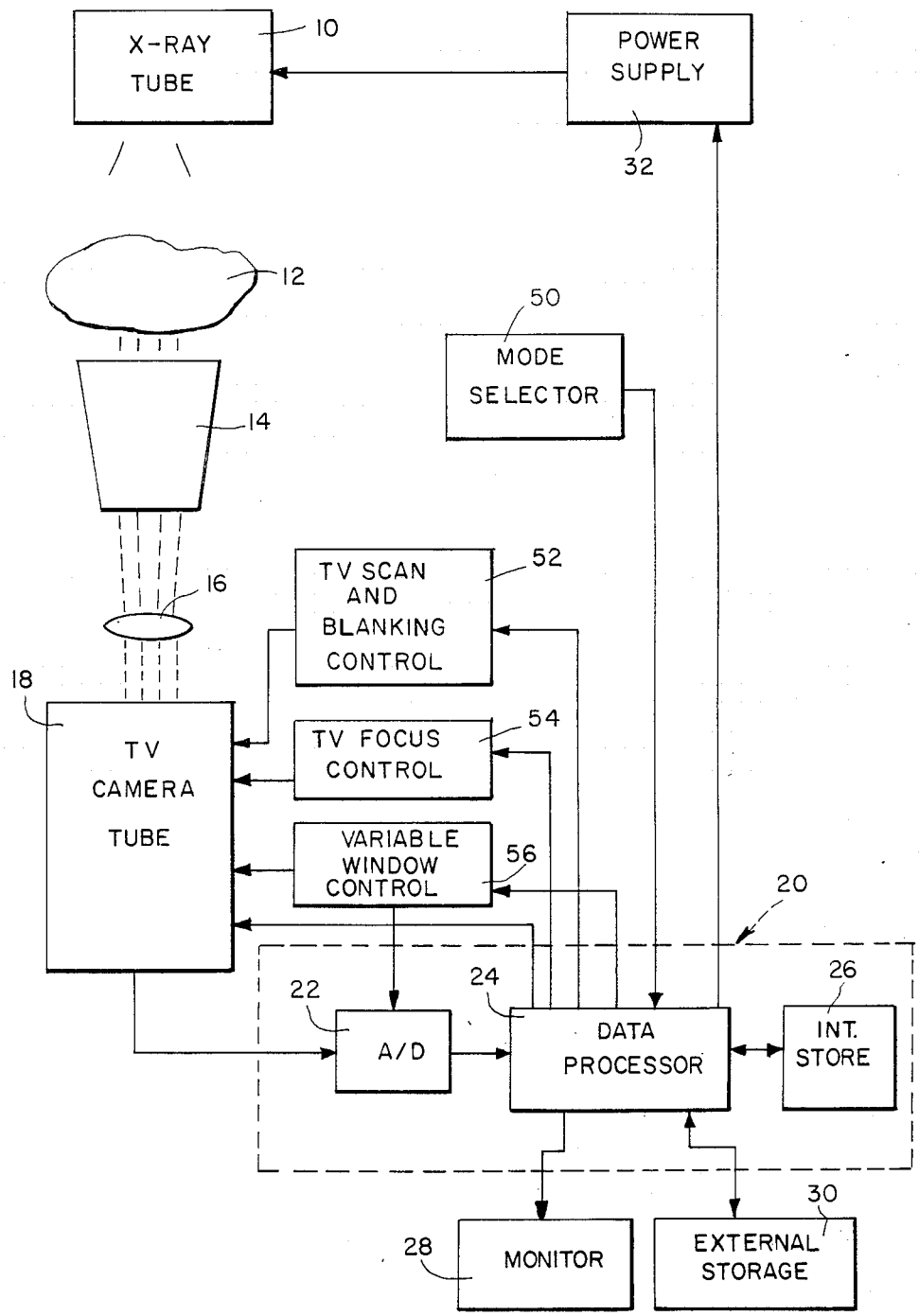
FIG. 4 is a diagram illustrating one form of apparatus constructed to operate in accordance with the present invention.

FIG. 4 is a block diagram illustrating one form of apparatus constructed to operate in accordance with the present invention as described above particularly with reference to FIG. 3. Thus, the apparatus illustrated in FIG. 4 comprises an X-ray tube 10 for exposing an object or subject 12 to the X-rays, which rays penetrate the subject and impinge on an image intensifier tube 14. The latter converts the X-rays to light rays which are transmitted via an optical system 16 onto the mosaic of a TV camera tube 18. The mosaic is scanned by the TV electron beam, and electrical signals representing frames of the object being imaged are read out to a digital processor system generally designated 20. The latter system includes an analog to digital (A/D) converter 22 which digitizes the electrical signals before transmitting them to a data processing unit 24 and memory 26 which process and store the data, in accordance wih conventional data processing systems used in digital fluorography. The digital system 20 may then output the processed information to a monitor 28 for display, or to an external storage device 30 for storage, also in accordance with conventional systems. The apparatus further includes an X-ray power supply 32 supplied with exposure pulses from the digital system 20.

The apparatus illustrated in FIG. 4 may include means enabling it to be operated according to the conventional continuous mode and/or the conventional pulsed mode, as illustrated in FIGS. 1 and 2, respectively. However, the illustrated apparatus also includes means enabling it to be operated according to the novel pulsed mode illustrated in FIG. 3, as well as in FIGS. 5 and 6 to be described below.

Thus, the illustrated apparatus may include a mode selector 50 which controls a TV blanking control unit 52 of the TV camera 18, so that when the novel pulse mode is selected, the blanking pulses applied to the TV camera are lengthened from about 1.6 ms (in the European system) to about 3.6 ms. As indicated earlier, this optional lengthening of the blanking pulse also decreases the number of active lines from 575/2 to 256, as illustrated in FIG. 3. The mode selector 50 also controls the X-ray power supply 32 causing same to produce an exposure pulse, of about 3 ms, within the extended time interval 3.6 ms of the blanking pulse, as indicated at 3a in FIG. 3. The control by selector 50 is via processor 24.

It will thus be seen that the system illustrated in FIG. 4 may be operated at substantially greater frame rates than the conventional pulsed mode systems illustrated in FIG. 2 in order to image moving objects without smear. Further, since the exposure is for a very short portion of each frame, larger dosages may be used than in the continuous mode illustrated in FIG. 1, thereby providing better contrast than possible when using the conventional continuous mode, as well as stopping action better than the continuous mode.

FIG. 4 also illustrates the option mentioned earlier of increasing the electron beam width in order to better assure removal of charges remaining on the target. Thus, as shown in FIG. 4, the mode selector 50 also controls, via processor 24, a focus control unit 54 which, when either the conventional pulsed modes illustrated in FIG. 2, or the novel pulsed mode illustrated in FIG. 3, is used, switches in (or switches out) an electrical resistor in the focusing coil circuit of the TV camera to increase the beam width during a 256 line mode.

The TV camera unit 18 and the digital processor system 20 may be commercially available equipment. One form of commercially available equipment includes a choice between a 9 bit analog to digital (A/D) converter 22, or an 8 bit analog to digital converter with a variable window. One source of noise in such a system is the digitization noise arising in the analog to digital converter; that is, the digitization noise in an 8 bit converter, having 256 levels, is substantially larger than that in a 9 bit or 10 bit converter.

We have found that the digitization noise can be substantially reduced by controlling the analog to digital converter 22 in accordance with the setting of the variable window. Thus, the system illustrated in FIG. 4 includes a variable window control unit 56 which is controlled by the setting of the variable window to control the analog to digital converter 22, to set the threshold and gain of the converter to include only signals of interest, thus increasing the effectiveness of the A/D conversion and effectively reducing the A/D digitization noise.

The above described arrangement results in an effective 256 line system, which is normally sufficient for ventricular cardiac imaging.

Figure 5:
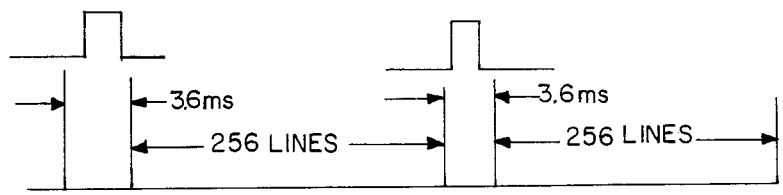
FIGS. 5 and 6 diagrammatically illustrate the operation of the apparatus in accordance with two variations.

An alternative form of the invention is illustrated in FIG. 5, in which a pulse of X-ray radiation is applied in each vertical sync (i.e. blanking or retrace) interval, but in which a Plumbicon tube is used. For a normal one inch Plumbicon tube, the second field will be only about 14% higher in magnitude than the first field. This variation can be compensated for either by a variable gain amplifier at the output of the TV camera tube (variations on a field to field basis), or by compensation in the data processor which receives the signals. This technique allows a pulsed 512 line readout, with a 3.6 ms extended effective vertical blanking interval, as shown in FIG. 5.

Figure 6:
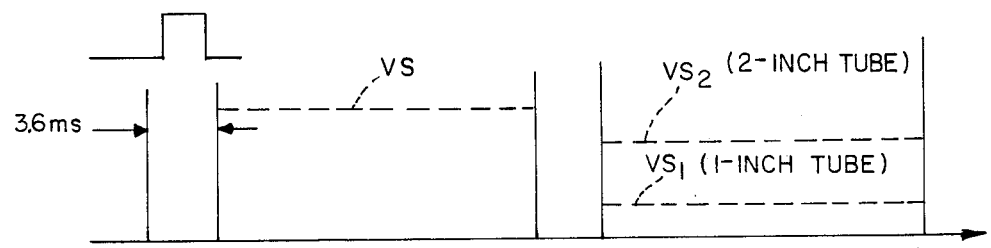

As a further alternative, the invention may utilize a two inch Plumbicon tube, instead of a normal one inch tube. If the beam diameter is kept small, the second field can be increased relative to its value in the one inch tube, and the compensation method of the FIG. 5 arrangement can be used. This variation is illustrated in FIG. 6, wherein VS. illustrates the video signal in the second field for a one inch tube, and VS. illustrates the corresponding signal in a two inch tube.

Figure 7:
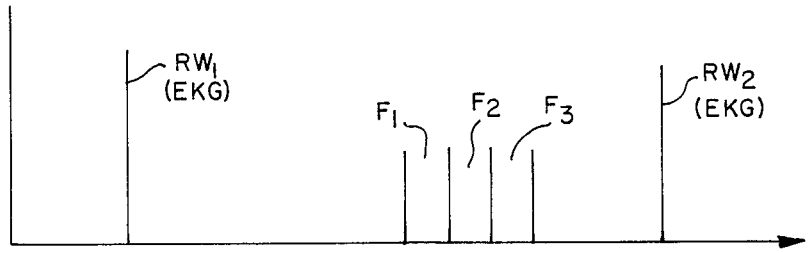
FIG. 7 is a diagram illustrating an advantage in the FIGS. 5 and 6 operation by allowing closely spaced frames within a longer interval, such as a heart cycle.

A particular advantage in the variations illustrated is that they permit the use of the standard interlaced mode of data acquisition, which simplifies system design. In addition, the invention allows closely spaced frames within a longer interval, such as for example in a heart cycle. This is particularly illustrated in the diagram of FIG. 7, wherein the R wave signals RW1, RW2, from the EKG, can be used for triggering the readout frames F1, F2 and F3. Thus, the radiation received by the subject may be for two or three frames (three frames being shown in FIG. 7) of 20 or so in a normal heart cycle. This permits the radiation dosage during each frame to be increased according to a factor of or approaching ten, over the radiation dosage permitted for a conventional continuous mode, without an increase in the overall radiation applied to the patient.

While the invention has been described with respect to several preferred embodiments, it will be appreciated that many other variations, modifications and applications of the invention may be made.

What is claimed is:

1. A system for converting video camera images obtained when the camera scans radiation images to frames of electrical signals, said radiation images obtained responsive to pulses applied to activate a radiation source during pulse periods, said system comprising:
    (a) means for applying said pulses at a rate of at least 15 pulses per second, and (b) means for reading out said frames at a rate of at least 15 per second.

2. The system of claim 1, wherein said rates of applying pulses is equal to or greater than 25 pps, and the rate of reading out said frames is equal to or greater than 25 per second.

3. The system of claim 2, wherein said camera scans during scanning periods, said system including means for applying said pulses during said scanning periods.

4. The system of claim 3, and means for applying said pulses at the beginning of said scanning periods.

5. An improved method of converting video camera images to electrical signals, said images having been obtained using radiation provided responsive to pulsing a radiation source, detecting the radiation from the source that traverses an object to provide images of the interior of the object, said camera scanning said images for a scan time period, said scan time period sufficient to enable the scanning to occur over N number of lines, said scanning providing frames of signals corresponding to said images, said improved method comprising the steps of:
(a) pulsing said source at a rate in excess of at least 15 and less than 50 pulses per second, and
(b) generating said frames at a rate at least equal to said source pulsing rate.

6. The method of the claim 5, wherein said scan time period is followed by a scrub period in which the image is scanned to scrub out the electrical charges obtained during the preceding scan time period.

7. The method according to claim 5, wherein the interval available for X-ray pulsing is increased from about 1.2 ms to about 3.5 ms.

8. The method of claim 5, comprising the step of: pulsing said source during a pulse period which is at least partly concurrent with said scan time period.

9. The method according to claim 8, wherein said scan time periods are effectively shortened and wherein the pulse period is lengthened to provide radiation for a period greater than the normal retrace period.

10. The method of claim 8, wherein said pulse period occurs at the start of said scan time period.

11. The method of claim 10, wherein a retrace blanking period occurs at least partially contemporaneously with said pulse period.

12. Apparatus for examining an object, comprising:
(a) a source of penetrating radiation;
(b) energizing means for energizing said source to expose the object to said radiation;
(c) a TV camera tube having a mosaic and means for generating an electron beam;
(d) converting means for converting the radiation transmitted through the object to a pattern of electrical charges on said mosaic;
(e) scanning means including the electron beam of the TV camera tube, for producing scanning signals responsive to the scanning by said electron beam of said target to thereby read out electrical signals representing frames of the object being examined;
(f) said scanning means including means for producing blanking signals for blanking the TV camera tube during retrace intervals between frames;
(g) said apparatus being characterized in that said energizing means are controlled by exposure pulses applied during retrace intervals concurrently with said blanking signals, and wherein said blanking signal intervals are shorter than the intervals of said scanning signals.

13. The apparatus according to claim 12 including means for controlling said scanning means to also scan said target to scrub out electrical charges of each read out field.

14. The apparatus according to claim 13 including means for controlling said scanning means to operate at scanning intervals which are effectively shorter than the conventional TV camera scanning intervals, and wherein said energizing means provides exposure pulses producing available exposure intervals equal to or greater than the retrace interval of conventional TV camera scanning systems.

15. The apparatus according to claim 14 wherein the available intervals are for periods of approximately 3.5 ms.

16. The apparatus according to claim 15 wherein the available interval is slightly greater than 3 ms, and the exposure pulses have a duration of approximately 3 ms.

17. The apparatus according to claim 16 wherein said source of penetrating radiation is an X-ray tube, and wherein said converting means for converting radiation to a pattern of electrical charges on the mosaic of the TV camera tube includes an image intensifier for converting the X-ray radiation to a light pattern which is projected on the surface of said mosaic.

18. The apparatus according to claim 17 further including
(a) an analog to digital converter for providing digital information;
(b) a processor for processing digital information; and
(c) a monitor.

19. The apparatus according to claim 18 wherein said scanning means scans 256 positions of the mosaic along 256 scanning lines, and said processor includes a 256×256 storage matrix.

20. The apparatus according to claim 18 wherein said scanning means scans 512 positions of said mosaic along 512 scanning lines, and said processor includes a 512×512 storage matrix.

21. The apparatus according to claim 18 wherein the analog to digital converter includes a variable window to enable varying the range of voltages digitized, and wherein the analog to digital converter is controlled by the setting of said variable window.

22. A method of examining an object by repeatedly exposing the same to a source of penetrating radiation, said method comprising the steps of:
(a) converting the radiation transmitted to the object to a pattern of electrical charges on the mosaic of a TV camera;
(b) scanning repeatedly said mosaic with an electron beam controlled by scanning signals to read out during scanning intervals electrical signals representing frames of the object examined;
(c) separating said scanning signals with blanking signals operating for intervals shorter than said scanning intervals for blanking the TV camera between readout frames; and
(d) energizing said source of penetrating radiation with exposure pulses applied during intervals at least partially concurrent with said blanking signals.

23. The method according to claim 22 wherein the step of scanning said mosaic by an electron beam to read out during scanning intervals electrical signals representing frames of the object examined is followed by the step of scrubbing said target during which the mosaic is scrubbed to scrub out the electrical charges of the preceding read out field.

24. The method according to claim 22 including the step of shortening the scanning intervals by applying the exposure pulses to the radiation source for an exposure period greater than normal retrace intervals of a conventional TV camera scanning system.

25. The method according to claim 22 including increasing the interval available for pulsing from about 1.2 ms to about 3.5 ms.

26. The method according to claim 25 including the step of increasing the available intervals to slightly more than 3 ms, and applying the exposure pulses for an exposure period of approximately 3 ms.

27. The method of claim 25, wherein said available interval during retrace and blanking signals for X-ray pulsing is about 3.6 ms.

28. The method according to claim 22 wherein the source of radiation is an X-ray tube, and including the steps of:
 (a) transmitting th X-rays through the object;
 (b) converting the X-rays that have passed through the object to light;
 (c) converting said light to a pattern of electrical charges on the mosaic of the TV camera tube;
 (d) scanning the mosaic to read out electrical signals;
 (e) digitizing the electrical signals read out from the TV camera tube;
 (f) processing said digitized read out signals; and
 (g) displaying the processed readout signals on a monitor.

29. The method according to claim 28 including the steps of:
 (a) reading out electrical signals of the TV camera tube by scanning 256 positions along 256 scanning lines; and
 (b) storing the digitized signals in a 256×256 storage matrix.

30. The method according to claim 28 including the steps of:
 (a) scanning 512 positions of the mosaic along 512 scanning lines; and
 (b) storing the digitized electrical signals in a 512×512 storage matrix.

31. The method according to claim 28 including the step of blocking the pulsing of the source of penetrating radiation during instances of maximum motion of the object being examined, when the object being examined is one which moves relatively quickly during part of an interval.

32. The method according to claim 28 including the step of windowing the digitized electrical signals readout of the TV camera tube to enable varying the range of the digitized signals.

33. The method according to claim 32 including the steps of varying the precision of the digitization of the analog signals by using a variable window and varying the window setting.

34. A system according to claim 1 wherein said means for applying said pulses applies the pulses at a rate less than about 50 pulses per second, and said means for reading out said frames reads out the frames at a rate less than about 60 frames per second.

* * * * *